United States Patent
Housman (10) Patent No.: US 9,924,934 B2
(45) Date of Patent: Mar. 27, 2018

(54) SURGICAL ANCHOR DELIVERY SYSTEM

(75) Inventor: Mark Edwin Housman, North Attleborough, MA (US)

(73) Assignee: Smith & Nephew, Inc., Memphis, TN (US)

( * ) Notice: Subject to any disclaimer, the term of this patent is extended or adjusted under 35 U.S.C. 154(b) by 65 days.

(21) Appl. No.: 14/123,713

(22) PCT Filed: Jun. 7, 2012

(86) PCT No.: PCT/US2012/041298
§ 371 (c)(1),
(2), (4) Date: Feb. 28, 2014

(87) PCT Pub. No.: WO2012/170662
PCT Pub. Date: Dec. 13, 2012

(65) Prior Publication Data
US 2014/0172016 A1    Jun. 19, 2014

Related U.S. Application Data

(60) Provisional application No. 61/494,273, filed on Jun. 7, 2011.

(51) Int. Cl.
*A61B 17/04* (2006.01)
*A61B 17/88* (2006.01)

(52) U.S. Cl.
CPC ...... *A61B 17/0401* (2013.01); *A61B 17/0483* (2013.01); *A61B 17/888* (2013.01); *A61B 2017/0409* (2013.01); *A61B 2017/0441* (2013.01)

(58) Field of Classification Search
CPC ........... A61B 17/0401; A61B 17/0483; A61B 17/888; A61B 2017/0409; A61B 2017/0441
See application file for complete search history.

(56) References Cited

U.S. PATENT DOCUMENTS

| | | | |
|---|---|---|---|
| 2,288,864 | A | 7/1942 | Whitehead et al. |
| 3,320,783 | A | 5/1967 | Kerr |
| 3,499,222 | A | 3/1970 | Linkow et al. |
| 3,716,058 | A | 2/1973 | Tanner |

(Continued)

FOREIGN PATENT DOCUMENTS

| | | |
|---|---|---|
| CN | 1701772 A | 11/2005 |
| CN | 1829479 A | 9/2006 |

(Continued)

OTHER PUBLICATIONS

Hunt, Patrick, D.V.M. et al. "Development of a Perforated Biodegradable Interference Screw", Arthroscopy: The Journal of Arthroscopic and Related Surgery, vol. 21, No. 3, Mar. 2005; pp. 258-265.

(Continued)

*Primary Examiner* — Julie A Szpira
(74) *Attorney, Agent, or Firm* — Burns & Levinson, LLP; Joseph M. Maraia (57) ABSTRACT

The present invention relates to a surgical anchor delivery system (10) including a delivery device (11) having a shaft (14) and a handle (13), an advancer (15) for advancing a surgical anchor (12) distally along the shaft (14); and a plurality of surgical anchors (12) loaded upon the shaft (14).

23 Claims, 9 Drawing Sheets

(56) References Cited

U.S. PATENT DOCUMENTS

| | | |
|---|---|---|
| 3,821,975 A | 7/1974 | Haker |
| 3,869,942 A | 3/1975 | DeCaro |
| 3,874,258 A | 4/1975 | Semola et al. |
| 4,027,572 A | 6/1977 | Burge |
| 4,177,797 A | 12/1979 | Baylis et al. |
| D288,777 S | 3/1987 | Kwon |
| 4,653,489 A | 3/1987 | Tronzo |
| 4,738,255 A | 4/1988 | Goble et al. |
| 4,741,651 A | 5/1988 | Despres |
| 4,834,757 A | 5/1989 | Brantigan |
| 4,854,311 A | 8/1989 | Steffee |
| RE33,114 E | 11/1989 | Chiavon |
| 4,913,143 A | 4/1990 | Oloff et al. |
| 4,961,740 A | 10/1990 | Ray et al. |
| 4,988,351 A | 1/1991 | Paulos et al. |
| 5,026,373 A | 6/1991 | Ray et al. |
| 5,055,104 A | 10/1991 | Ray |
| 5,116,337 A | 5/1992 | Johnson |
| 5,129,904 A | 7/1992 | Illi |
| 5,129,906 A | 7/1992 | Ross et al. |
| 5,139,520 A | 8/1992 | Rosenberg |
| 5,197,967 A | 3/1993 | Wilson |
| 5,236,431 A | 8/1993 | Gogolewski et al. |
| 5,242,447 A | 9/1993 | Borzone |
| 5,354,299 A | 10/1994 | Coleman |
| 5,364,400 A | 11/1994 | Rego, Jr. et al. |
| 5,370,662 A | 12/1994 | Stone et al. |
| 5,383,878 A | 1/1995 | Roger et al. |
| 5,407,427 A | 4/1995 | Zhu et al. |
| 5,411,506 A | 5/1995 | Goble et al. |
| 5,411,523 A | 5/1995 | Goble |
| 5,423,823 A | 6/1995 | Schmieding |
| 5,447,533 A | 9/1995 | Vachon et al. |
| 5,464,427 A | 11/1995 | Curtis et al. |
| 5,470,334 A | 11/1995 | Ross et al. |
| 5,531,780 A | 7/1996 | Vachon |
| 5,571,139 A | 11/1996 | Jenkins, Jr. |
| 5,573,548 A | 11/1996 | Nazre et al. |
| 5,593,409 A | 1/1997 | Michelson |
| 5,609,635 A | 3/1997 | Michelson |
| 5,626,613 A | 5/1997 | Schmieding |
| 5,632,747 A | 5/1997 | Scarborough |
| 5,645,547 A | 7/1997 | Coleman |
| 5,658,285 A | 8/1997 | Marnay et al. |
| 5,676,545 A | 10/1997 | Jones |
| 5,681,352 A | 10/1997 | Clancy, III et al. |
| 5,688,285 A | 11/1997 | Yamada |
| 5,690,676 A | 11/1997 | Dipoto et al. |
| 5,695,497 A | 12/1997 | Stahelin |
| 5,702,397 A | 12/1997 | Goble et al. |
| 5,709,683 A | 1/1998 | Bagby |
| 5,802,794 A | 9/1998 | Robson |
| 5,833,715 A | 10/1998 | Vachon et al. |
| 5,876,405 A | 3/1999 | Del Rio |
| 5,888,227 A | 3/1999 | Cottle |
| 5,891,146 A | 4/1999 | Simon et al. |
| 5,921,982 A | 7/1999 | Lesh et al. |
| 5,951,560 A | 9/1999 | Simon et al. |
| 5,961,524 A | 10/1999 | Crombie |
| 5,964,783 A | 10/1999 | Grafton et al. |
| 5,968,047 A | 10/1999 | Reed |
| 5,968,098 A | 10/1999 | Winslow |
| 5,984,967 A | 11/1999 | Zdeblick et al. |
| 6,008,433 A | 12/1999 | Stone |
| 6,039,762 A | 3/2000 | McKay |
| 6,086,593 A | 7/2000 | Bonutti |
| 6,096,060 A | 8/2000 | Fitts et al. |
| 6,097,986 A | 8/2000 | Janke et al. |
| 6,302,632 B1 | 1/2001 | Lin |
| 6,196,780 B1 | 3/2001 | Wakai et al. |
| 6,214,031 B1 | 4/2001 | Schmieding et al. |
| 6,235,057 B1 | 5/2001 | Roger et al. |
| 6,283,973 B1 | 9/2001 | Hubbard et al. |
| 6,360,129 B1 | 3/2002 | Ley et al. |
| 6,443,989 B1 | 9/2002 | Jackson |
| 6,447,545 B1 | 9/2002 | Bagby |
| 6,488,683 B2 | 12/2002 | Lieberman |
| 6,503,251 B1 | 1/2003 | Shadduck |
| 6,511,499 B2 | 1/2003 | Schmieding et al. |
| 6,514,257 B2 | 2/2003 | Dovesi et al. |
| 6,517,542 B1 | 2/2003 | Papay et al. |
| 6,527,774 B2 | 3/2003 | Lieberman |
| 6,544,265 B2 | 4/2003 | Lieberman |
| 6,551,319 B2 | 4/2003 | Lieberman |
| 6,551,320 B2 | 4/2003 | Lieberman |
| 6,551,322 B1 | 4/2003 | Lieberman |
| 6,554,830 B1 | 4/2003 | Chappius |
| 6,656,183 B2 | 5/2003 | Colleran et al. |
| 6,589,245 B1 | 7/2003 | Weiler et al. |
| 6,604,945 B1 | 8/2003 | Jones |
| 6,626,917 B1 | 9/2003 | Craig |
| 6,626,971 B1 | 9/2003 | Craig |
| 6,648,903 B1 | 11/2003 | Pierson |
| 6,685,728 B2 | 2/2004 | Sinnott et al. |
| 6,823,871 B2 | 11/2004 | Schmieding |
| 6,855,168 B2 | 2/2005 | Crozet |
| 6,863,671 B1 | 3/2005 | Strobel et al. |
| 6,942,669 B2 | 9/2005 | Kurc |
| 6,953,462 B2 | 10/2005 | Lieberman |
| 7,033,372 B1 | 4/2006 | Cahalan |
| 7,070,586 B2 | 7/2006 | Hart et al. |
| 7,083,647 B1 | 8/2006 | Sklar et al. |
| 7,090,690 B2 | 8/2006 | Foerster et al. |
| 7,189,251 B2 | 3/2007 | Kay |
| 7,195,634 B2 | 3/2007 | Schmieding et al. |
| 7,217,279 B2 | 5/2007 | Reese |
| 7,322,978 B2 | 1/2008 | West |
| 7,322,986 B2 | 1/2008 | Wolf |
| 7,594,929 B2 | 9/2009 | Collette |
| 7,608,098 B1 | 10/2009 | Stone et al. |
| 7,867,252 B2 | 1/2011 | Criscuolo et al. |
| 7,883,529 B2 | 2/2011 | Sinnott et al. |
| 7,914,539 B2 | 3/2011 | Stone et al. |
| 8,016,865 B2 | 9/2011 | Donnelly et al. |
| 8,034,090 B2 | 10/2011 | Stone et al. |
| 8,167,906 B2 | 5/2012 | Cauldwell et al. |
| 8,343,186 B2 | 1/2013 | Dreyfuss et al. |
| 8,597,328 B2 | 12/2013 | Cauldwell et al. |
| 8,623,052 B2 | 1/2014 | Dreyfuss et al. |
| 8,636,799 B2 | 1/2014 | Sklar et al. |
| 8,672,967 B2 | 3/2014 | DiMatteo et al. |
| 8,801,755 B2 | 5/2014 | Dreyfuss et al. |
| 8,821,541 B2 | 9/2014 | Dreyfuss et al. |
| 8,979,865 B2 | 3/2015 | Fan et al. |
| 9,155,531 B2 | 10/2015 | Housman |
| 9,308,080 B2 | 4/2016 | Housman et al. |
| 9,393,006 B2 | 7/2016 | Housman et al. |
| 9,427,270 B2 | 8/2016 | Housman |
| 9,526,488 B2 | 12/2016 | Arai et al. |
| 9,579,188 B2 | 2/2017 | Bowman et al. |
| 2002/0022862 A1 | 2/2002 | Grafton et al. |
| 2002/0052629 A1 | 5/2002 | Morgan et al. |
| 2002/0055737 A1 | 5/2002 | Lieberman |
| 2002/0055738 A1 | 5/2002 | Lieberman |
| 2002/0055742 A1 | 5/2002 | Lieberman |
| 2002/0087189 A1 | 7/2002 | Bonutti |
| 2002/0087190 A1 | 7/2002 | Benavitz et al. |
| 2002/0099382 A1 | 7/2002 | Salazar et al. |
| 2002/0111653 A1 | 8/2002 | Foerster |
| 2002/0143335 A1 | 10/2002 | von Hoffmann et al. |
| 2002/0165546 A1 | 11/2002 | Goble et al. |
| 2003/0055431 A1 | 3/2003 | Brannon |
| 2003/0065361 A1 | 4/2003 | Dreyfuss |
| 2003/0065374 A1 | 4/2003 | Honeck |
| 2003/0069640 A1 | 4/2003 | Ferreira et al. |
| 2003/0125749 A1 | 7/2003 | Yuan et al. |
| 2003/0181913 A1 | 9/2003 | Lieberman |
| 2003/0195529 A1 | 10/2003 | Takamoto et al. |
| 2004/0015170 A1 | 1/2004 | Tallarida et al. |
| 2004/0030343 A1 | 2/2004 | Kurc |
| 2004/0039404 A1 | 2/2004 | Dreyfuss |
| 2004/0073216 A1 | 4/2004 | Lieberman |
| 2004/0093032 A1 | 5/2004 | Sinnott et al. |
| 2004/0097945 A1 | 5/2004 | Wolf |

(56) References Cited

U.S. PATENT DOCUMENTS

| | | |
|---|---|---|
| 2004/0122424 A1 | 6/2004 | Ferree |
| 2004/0143158 A1 | 7/2004 | Hart et al. |
| 2004/0143237 A1 | 7/2004 | Hart et al. |
| 2004/0153074 A1* | 8/2004 | Bojarski ............ A61B 17/0401 606/232 |
| 2004/0267265 A1 | 12/2004 | Kyle |
| 2005/0107828 A1 | 5/2005 | Reese |
| 2005/0159727 A1 | 7/2005 | Lesh |
| 2005/0222681 A1 | 10/2005 | Richley et al. |
| 2005/0234458 A1 | 10/2005 | Huebner |
| 2005/0250984 A1 | 11/2005 | Lam et al. |
| 2005/0250985 A1 | 11/2005 | Saadat et al. |
| 2005/0250987 A1 | 11/2005 | Ewers et al. |
| 2005/0250988 A1 | 11/2005 | Ewers et al. |
| 2005/0267478 A1* | 12/2005 | Corradi ............... A61B 17/064 606/916 |
| 2005/0283239 A1 | 12/2005 | Crozet |
| 2006/0009769 A1 | 1/2006 | Lieberman |
| 2006/0030948 A1 | 2/2006 | Manrique et al. |
| 2006/0079895 A1 | 4/2006 | McLeer |
| 2006/0100627 A1 | 5/2006 | Stone et al. |
| 2006/0106390 A1 | 5/2006 | Jensen et al. |
| 2006/0142769 A1 | 6/2006 | Collette |
| 2006/0149266 A1 | 7/2006 | Cordasco |
| 2006/0217681 A1 | 9/2006 | Hart et al. |
| 2006/0241636 A1 | 10/2006 | Novak et al. |
| 2006/0247642 A1 | 11/2006 | Stone et al. |
| 2006/0253080 A1 | 11/2006 | Tulleken et al. |
| 2006/0276841 A1 | 12/2006 | Barbieri et al. |
| 2007/0032797 A1 | 2/2007 | Ortiz et al. |
| 2007/0093895 A1 | 4/2007 | Donnelly et al. |
| 2007/0122764 A1 | 5/2007 | Balfour et al. |
| 2007/0142849 A1 | 6/2007 | Ewers et al. |
| 2007/0185532 A1 | 8/2007 | Stone et al. |
| 2007/0198019 A1 | 8/2007 | Schomer et al. |
| 2008/0027446 A1 | 1/2008 | Stone et al. |
| 2008/0065114 A1 | 3/2008 | Stone et al. |
| 2008/0082128 A1 | 4/2008 | Stone |
| 2008/0132932 A1 | 6/2008 | Hoeppner |
| 2008/0140092 A1 | 6/2008 | Stone et al. |
| 2008/0140093 A1 | 6/2008 | Stone et al. |
| 2008/0154314 A1 | 6/2008 | McDevitt |
| 2008/0179839 A1 | 7/2008 | Walters |
| 2008/0275431 A1 | 11/2008 | Stone et al. |
| 2009/0024174 A1 | 1/2009 | Stark |
| 2009/0042951 A1 | 2/2009 | Danziger |
| 2009/0076544 A1 | 3/2009 | DiMatteo et al. |
| 2009/0248029 A1 | 10/2009 | Paulos |
| 2009/0319043 A1 | 12/2009 | McDevitt et al. |
| 2010/0106166 A1* | 4/2010 | Cropper ............ A61B 17/0057 606/139 |
| 2011/0054526 A1 | 3/2011 | Stone et al. |
| 2011/0112576 A1* | 5/2011 | Nguyen ............. A61B 17/0401 606/232 |
| 2011/0224727 A1 | 9/2011 | Housman et al. |
| 2011/0282450 A1 | 11/2011 | Donnelly et al. |
| 2011/0319933 A1 | 12/2011 | Tepic |
| 2012/0059384 A1 | 3/2012 | Fan et al. |
| 2012/0179163 A1 | 7/2012 | Housman et al. |
| 2013/0150859 A1 | 6/2013 | Kehres et al. |
| 2013/0158596 A1 | 6/2013 | Miller et al. |
| 2013/0158597 A1 | 6/2013 | Hernandez |
| 2013/0158598 A1 | 6/2013 | Lizardi |
| 2013/0158599 A1 | 6/2013 | Hester et al. |
| 2013/0158610 A1 | 6/2013 | Hernandez |
| 2013/0178901 A1 | 7/2013 | Arai et al. |
| 2014/0081339 A1 | 3/2014 | Bowman et al. |
| 2014/0142697 A1 | 5/2014 | Sklar et al. |
| 2014/0148850 A1 | 5/2014 | DiMatteo et al. |
| 2014/0172016 A1 | 6/2014 | Housman |
| 2014/0277129 A1 | 9/2014 | Arai et al. |
| 2014/0277130 A1 | 9/2014 | Housman |
| 2014/0277192 A1 | 9/2014 | Housman |
| 2015/0196388 A1 | 7/2015 | Housman et al. |
| 2015/0327984 A1 | 11/2015 | Arai et al. |
| 2016/0235399 A1 | 8/2016 | Housman et al. |
| 2016/0374661 A1 | 12/2016 | Housman et al. |
| 2017/0014224 A1 | 1/2017 | Arai et al. |
| 2017/0020589 A1 | 1/2017 | Bowman et al. |
| 2017/0049438 A1 | 2/2017 | Arai et al. |

FOREIGN PATENT DOCUMENTS

| | | |
|---|---|---|
| CN | 101031248 A | 9/2007 |
| CN | 101422381 A | 5/2009 |
| CN | 101573078 A | 11/2009 |
| CN | 201436022 U | 4/2010 |
| CN | 102068305 A | 5/2011 |
| CN | 101573078 B | 10/2011 |
| CN | 102512253 A | 6/2012 |
| CN | 102525583 A | 7/2012 |
| CN | 102551821 A | 7/2012 |
| CN | 102905636 A | 1/2013 |
| EP | 05202698 A1 | 9/1992 |
| EP | 0538895 A2 | 4/1993 |
| EP | 0682917 B1 | 11/1995 |
| EP | 0686373 A1 | 12/1995 |
| EP | 0502698 B1 | 11/1997 |
| EP | 0669110 B1 | 5/2000 |
| EP | 0686373 B1 | 3/2001 |
| EP | 1147751 B1 | 10/2001 |
| EP | 1093774 B1 | 6/2002 |
| EP | 1234637 A2 | 8/2002 |
| EP | 0796593 B1 | 5/2004 |
| EP | 1430843 A2 | 6/2004 |
| EP | 1917926 A1 | 5/2008 |
| EP | 2036501 A3 | 3/2009 |
| EP | 1917926 B1 | 11/2009 |
| EP | 2422711 A2 | 2/2012 |
| EP | 2422712 A1 | 2/2012 |
| EP | 2422712 A2 | 2/2012 |
| EP | 2596758 A1 | 5/2013 |
| EP | 2601894 A1 | 6/2013 |
| FR | 2760355 A1 | 9/1998 |
| FR | 2803739 A1 | 7/2001 |
| FR | 2846867 A1 | 5/2004 |
| FR | 2879915 A1 | 6/2006 |
| GB | 2294399 A | 5/1996 |
| JP | H10-000200 | 1/1998 |
| JP | H10200 A | 1/1998 |
| JP | 2005-529650 | 10/2005 |
| JP | 2006212449 A | 8/2006 |
| JP | 2006-305348 A | 11/2006 |
| WO | 199608205 A1 | 3/1996 |
| WO | 199619947 A1 | 7/1996 |
| WO | 199802117 A1 | 1/1998 |
| WO | 199826717 A1 | 6/1998 |
| WO | 03063713 A1 | 8/2003 |
| WO | 03103507 A2 | 12/2003 |
| WO | 2006055516 A2 | 5/2006 |
| WO | 2007093192 A1 | 8/2007 |
| WO | 2008021474 A2 | 2/2008 |
| WO | 20081009944 A1 | 8/2008 |
| WO | 2009042951 A1 | 4/2009 |
| WO | 2010009217 A1 | 1/2010 |
| WO | 2010017631 A1 | 2/2010 |
| WO | 2010053708 A1 | 5/2010 |
| WO | 2011059995 A2 | 5/2011 |
| WO | 2011060022 A2 | 5/2011 |
| WO | 2011112776 A1 | 9/2011 |

OTHER PUBLICATIONS

International Search and Written Opinion for PCT/US2011/027837 dated May 19, 2011.

Smith & Nephew brochure titled "Bio RCITM Bioabsorbable Screws: Anatomically Targeted Screws for ACL and PCL Reconstruction", 2000.

Biomet brochure "Bio-CoreTM Interference Screw", 2007.

International Search and Written Opinion for PCT/US2009/065304 dated Jun. 5, 2013.

International Search and Written Opinion for PCT/US2012/041298 dated Jun. 5, 2013.

(56) References Cited

OTHER PUBLICATIONS

International Search and Written Opinion for PCT/US2012/028803 dated Oct. 24, 2010.
Notice of Reasons for Rejections for Japanese Patent Application No. 2011-538642, dated Oct. 1, 2013.
First Office Action for Chinese Patent Application No. 200980155954.7, dated Apr. 12, 2013.
Second Office Action for Chinese Patent Application No. 200980155954.7, dated Oct. 24, 2013.
Notice of Reasons for Rejection for Japanese Patent Application No. 2012-557236 dated Mar. 2, 2015.
Patent Examination Report No. 1 for Australian Patent Application No. 2011224326 dated Apr. 21, 2015.
Second Office Action for Chinese Patent Application No. 201180013194.3, dated Mar. 23, 2015.
First Office Action for Chinese Patent Application No. 201280022627.6, dated Apr. 13, 2015.
International Search and Written Opinion for PCT/US2014/033535 dated Jul. 18, 2014.
International Search and Written Opinion for PCT/US2014/022539 dated Jun. 27, 2014.
International Search and Written Opinion for PCT/US2014/020747 dated Jun. 6, 2014.
Decision of Rejections for Japanese Patent Application No. 2011-538642, dated Jun. 2, 2014.
First Office Action for Chinese Patent Application No. 201180013194.3, dated Jul. 21, 2014.
Notice of Reasons for Rejection for Japanese Patent Application No. 2012-557236 dated Nov. 25, 2014.
Patent Examination Report No. 1 for Australian Patent Application No. 2009319879 dated Nov. 10, 2014.
International Search and Written Opinion for PCT/US2014/066389 dated Feb. 17, 2015.
Substantive Examination Report from related Mexico Patent Application No. MX/a/2013/010383 dated Jan. 19, 2016.
Communication from related European Patent Application No. 09761114.9 dated Dec. 3, 2015.
Communication from related European Patent Application No. 11710940.5 dated Dec. 8, 2015.
First Office Action for related Chinese Patent Application No. 201280038677.3 dated Sep. 6, 2015.
Substantive Examination of related Russian Application No. 2013144961/14(069526) dated Dec. 23, 2015.
Second Office Action for related Chinese Patent Application No. 201280022627.6 dated Sep. 16, 2015.
Substantive Examination for related Mexican Patent Application No. MX/a/2013/010383 dated Aug. 12, 2015.
Patent Examination Report No. 1 for related Australian Patent Application No. 2012229152 dated Aug. 18, 2015.
Third Office Action for related Chinese Patent Application No. 2011-80013194.3 dated Aug. 21, 2015.
International Preliminary Report on Patentability for related International Application No. PCT/US2014/033535, dated Oct. 22, 2015.
Decision of Rejection on related Japanese Patent Application No. 2012-557236 dated Oct. 9, 2015.
Patent Examination Report No. 1 for related Australian Patent Application No. 2012267924 dated Dec. 22, 2015.
Notice of Reasons for Rejection for related Japanese Application No. 2013-558094 dated Feb. 2, 2016.
Third Office Action from related Chinese Patent Application No. 201280022627.6 dated Mar. 4, 2016.
Second Office Action from related Chinese Application No. 201280038677.3 dated May 5, 2016.
Notice of Reasons for Rejection from related Japanese Application No. 2014-514625 dated Jun. 13, 2016.
International Preliminary Report on Patentability from related PCT Application No. PCT/US2014/066389 dated May 24, 2016.
Office Action from related Mexican Application No. MX/a/2013/010383 dated May 3, 2016.
Office Action and Search Report from related Chinese Application No. 201480032876.2 dated Oct. 19, 2016.
Office Communication from related European Application No. 14712930.8-1662 dated Nov. 24, 2016.
Communication from EPO from related European Application No. 12711719.0-1666 dated Jul. 28, 2016.
First Office Action from related Chinese Application No. 201480012203.0 dated Aug. 17, 2016.
Office Action from related Russian Application No. 2015147534/20(073143) dated Jun. 29, 2016.
Office Action from related Japanese Application No. 2013-558094 dated Sep. 5, 2016.
Communication from related European Application No. 12711719.0-1666 dated Jul. 28, 2016.
Office Action from related EPO Application No. 14716107.9-1664 dated Mar. 23, 2017.
Office Action from related Russian Application No. 2016124173/20(037886) dated Jan. 19, 2017.
Office Action from related Chinese Application No. 201280038677.3 dated Nov. 28, 2016.
Office Action from related Japanese Application No. 2014-514625 dated Dec. 19, 2016.

\* cited by examiner

SURGICAL ANCHOR DELIVERY SYSTEM

RELATED APPLICATIONS

This application is the U.S. National Stage of International Application No. PCT/US12/41298, filed on Jun. 7, 2012, which claims priority to and the full benefit of U.S. Provisional Application Ser. No. 61/494,273, filed Jun. 7, 2011, the entire contents of which are incorporated herein by reference.

The present invention relates to surgical instrument, and more particularly to surgical instrument for delivering surgical anchors.

Surgical anchors are typically supplied with a single-use disposable delivery device, with each anchor delivery system including a delivery device pre-loaded with a single anchor. Frequently, a surgical procedure will involve the use of two or more surgical anchors, necessitating the use of several delivery devices. However, from a procedural perspective this is both inefficient and expensive since for most anchor delivery systems, the bulk of the costs are attributable to the cost of the disposable delivery device, and not the anchor itself. Therefore, a more cost effective and procedurally efficient approach is desirable.

In its broadest sense the present invention provides a surgical anchor delivery system including a delivery device having an elongate shaft coupled with a handle, and means for advancing a surgical anchor distally along the shaft; and a plurality of surgical anchors loaded upon the shaft of the delivery device.

According to an aspect of the present invention there is provided a surgical anchor delivery system including a delivery device having an elongate shaft coupled with a handle, and an advancer for advancing a surgical anchor distally along the shaft; and a plurality of surgical anchors loaded upon the shaft.

Suitably, the plurality of surgical anchors consists of two, three, four, five or more anchors, which are loaded in series upon the elongate shaft.

The surgical anchors may be fenestrated or non-fenestrated.

Preferably, the surgical anchors are loaded with suture. Suitably, each surgical anchor is loaded with two or more sets of suture.

Optionally, the surgical anchors are connected to each other by suture. The suture may be adjustable and include a slip-knot.

Preferably, at least one of the plurality of surgical anchors includes a lumen which extends through a longitudinal axis of the anchor. This arrangement allows the anchor to be slidably mounted on the delivery device shaft, which passes through the anchor lumen so that the entire anchor is mounted on the shaft. Suitably, all of the plurality of surgical anchors include a lumen which extend through a longitudinal axis of each anchor. Alternatively, one of the plurality of surgical anchors includes a closed distal end and a lumen which partially extends through the anchor along its longitudinal axis. Suitably, the closed distal end is tapered; preferably, to a point. In this alternative embodiment, the remaining anchors of the plurality of surgical anchors all include a lumen which extends through a longitudinal axis of the anchor. Those anchors are slidably mounted upon the delivery device shaft, and the anchor having the closed distal end is mounted on the distal tip of the delivery device shaft.

Preferably, at least a distal region of the delivery device shaft has a non-circular cross section. Suitably, at least a distal region of the shaft has a hexagonal cross-section. Alternatively, the shaft has a generally circular cross-section and includes one or more cut-out regions formed by longitudinal grooves in the shaft surface. Suitably, the longitudinal grooves are formed in the distal region of the shaft and extend proximally along at least part of the length of the shaft. This prevents anchors possessing a lumen and loaded on the delivery device from rotating relative to the shaft. As a result, the delivery device can be used to rotationally advance the anchors into tissue.

Optionally, the delivery device shaft includes a lumen. The lumen may be axial or offset from the longitudinal axis of the shaft. Alternatively or additionally, the delivery device shaft includes one or more longitudinal slots in its outer surface. For example, the shaft may include one, two, three, four or more of such slots. In embodiments featuring a lumen and slots, the slot or slots are connected with the lumen. The purpose of the above features is to permit channelling of suture, which may be attached to one or more of the surgical anchors, through at least a portion of the device, and to exit in the handle region. Such features help to prevent snagging of the suture in the surgical site. In alternative embodiments, described in greater detail below, the advancer is a tubular member or sleeve, slidably mounted upon the shaft, and the suture can be threaded between the advancer sleeve and the shaft. According to this alternative embodiment, the shaft and or sleeve may contain a channel or groove respectively in their outer or inner surfaces to accommodate the suture and to prevent snagging between the shaft and sleeve.

Suitably, the delivery device shaft includes a pointed distal tip. Suitably, the pointed distal tip is sharpened or blunted. Suitably, the distal tip includes a threaded region. The tip can be used to prepare a small pilot hole prior to rotatably driving or pounding the anchor directly into bone.

Suitably, the advancer is a tubular member or sleeve mounted on the delivery device shaft. Suitably, the advancer is mounted proximally of, and its distal end abuts against, the most-proximal surgical anchor loaded on the device shaft. Suitably, the advancer includes means for advancing the tubular member or sleeve distally. Suitably, the advancer includes a knob mounted rotationally on the shaft. Suitably, the tubular member or sleeve includes a threaded proximal region and the knob includes means for engaging the threaded proximal region. Alternatively, the tubular member or sleeve is coupled to an adaptor at its proximal end or at a proximal region, and the adaptor includes threaded portion which is engageable with the threaded proximal region of the knob. Such arrangement provides that when the knob is rotated in a first direction, the tubular member or sleeve advances distally relative to the shaft. Optionally, the knob may rotate in a second direction, opposite to the first direction, to retract the tubular member or sleeve proximally relative to the shaft.

Alternatively, the tubular member or sleeve is coupled to a pin or tab. The pin or tab may be coupled with an indexer which enables predefined distal advancement of the tubular member or sleeve. For example, the delivery device shaft may include one or more detents or apertures for receipt of the pin or tab which is coupled with, and moveable relative to, the sleeve. The pin or tab can be moved to engage and disengage with the detents or apertures. The advancer may also include a handle or knob for controlling movement of the sleeve relative to the shaft; or the knob can be formed with the pin and tab to engage/disengage the pin or tab with the detents or apertures and also advance the sleeve relative to the shaft. Further alternatively, the tubular member or sleeve includes a series of apertures in its wall, which extend at least partially along its length, and the delivery device shaft includes one or more sprung pins for engagement with one or more of the apertures. For example, each of the one or more sprung pins is biased radially outwards and engages with an aperture of the sleeve. In order to advance the sleeve, the biased pin is compressed to disengage it from the aperture, the sleeve is moved distally, and the compressive force on the pin is removed once the sleeve has been advanced to a position where the pin can engage another aperture in the sleeve wall. The advancer can also include a ratchet mechanism for distally advancing the tubular member or sleeve.

In use, the tubular member or sleeve abuts against the proximal end of the most proximal of the plurality of surgical anchors. When the distal-most anchor has been deployed, the tubular member or sleeve is moved distally to advance the remaining anchor or anchors loaded on the delivery device shaft to a position where the most-distal anchor is at the distal end of the delivery device shaft and ready for deployment. This process can be repeated until all the anchors have been deployed.

Further alternatively, the advancer is a rod which is moveable within a longitudinal channel formed within the delivery device shaft. Suitably, the rod includes a radially extending pin which projects from the longitudinal channel. Suitably, the pin abuts against the proximal end of the most proximal of the plurality of surgical anchors, and is used to advance distally any surgical anchors which remain on the delivery device shaft after the distal most surgical anchor has been deployed. Suitably, the advancer includes a knob mounted rotationally on the shaft. Suitably, the rod includes a threaded proximal region and the knob includes means for engaging the threaded proximal region. Such arrangement provides that when the knob is rotated in a first direction, the rod advances distally relative to the shaft. The rod can be moved to advance the surgical anchors by any other suitable mechanisms, including those described above in relation to the sleeve.

Preferably, the handle includes one or more suture cleats.

The above and other aspects of the invention will now be described with reference to the following drawings in which.

Figure 1:
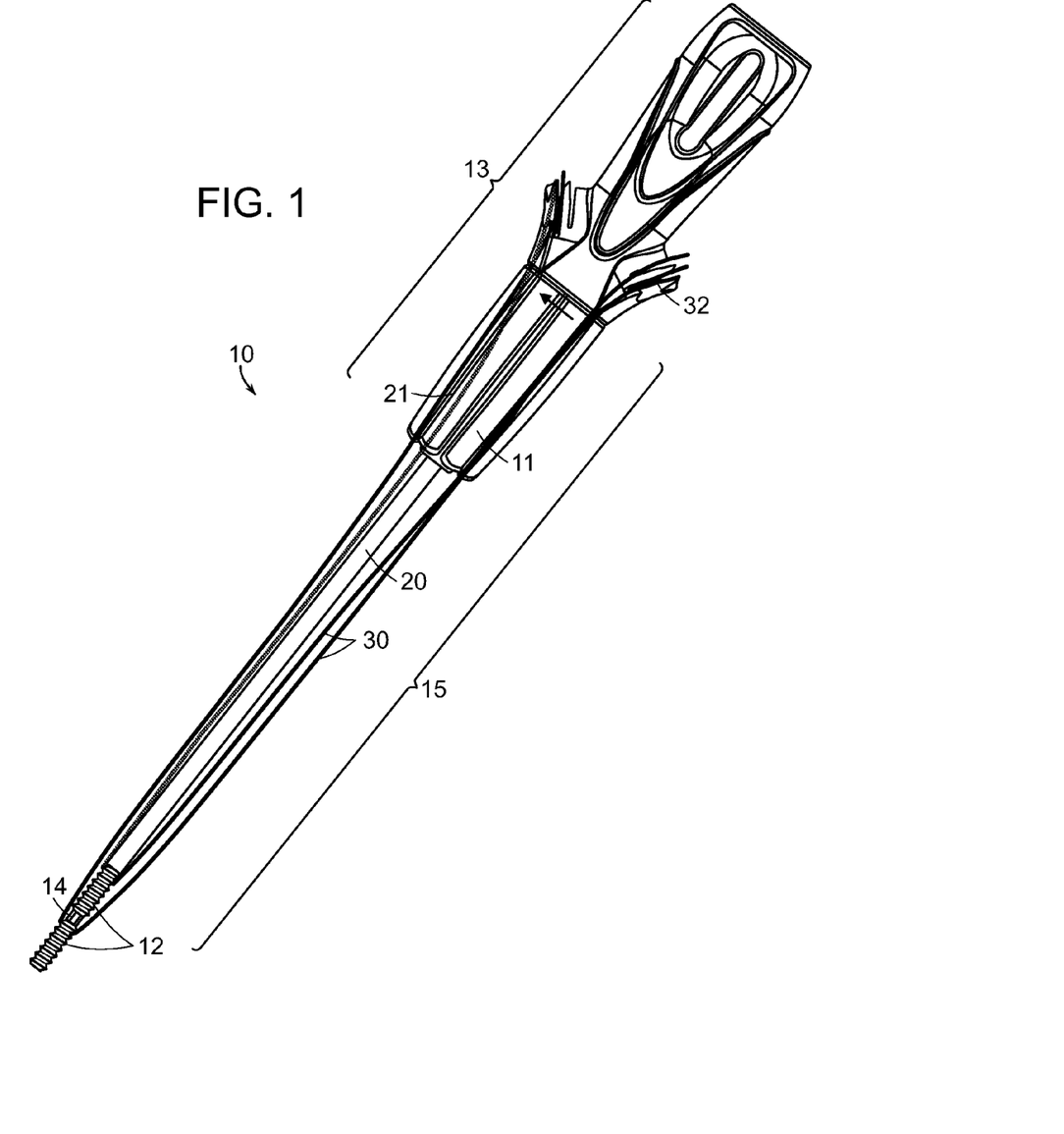
FIG. 1 is a side view of a surgical anchor delivery system according to a first embodiment of the invention.

Referring to FIG. 1 there is shown surgical anchor delivery system 10 formed of a delivery device 11 and two more surgical anchors in the form of suture anchors 12. The delivery device 11 includes a proximal handle 13 having a shaft 14 extending therefrom, two suture anchors 12 mounted in series at the distal end of shaft 14, and a mechanism 15 for advancing the anchors distally.

Mechanism 15 is formed from a sleeve 20 and driver 21. Sleeve 20 is slidably mounted on shaft 14 and has a distal end which abuts against the proximal-most surgical anchor. Driver 21 is formed with handle 13 and is rotationally mounted upon shaft 14, and in use can be actuated to advance sleeve 20 distally to move the proximal-most anchor into a position suitable for deployment, once the distal-most anchor has been deployed. This process will be described in greater detail below, with reference to FIGS. 4 to 6.

In FIG. 1, and the further Figures illustrating the invention, a gap is depicted between successive anchors. This is entirely for illustrative purposes to indicate the presence of multiple anchors. In practice, the anchors abut against each other, as shown in the close-up view of FIG. 2, which prevents the distal-most anchor from sliding back proximally during its deployment.

The illustrated embodiments are generally depicted as including two surgical anchors. However, the system can be preloaded with three, four, five or more surgical anchors.

Figure 2:
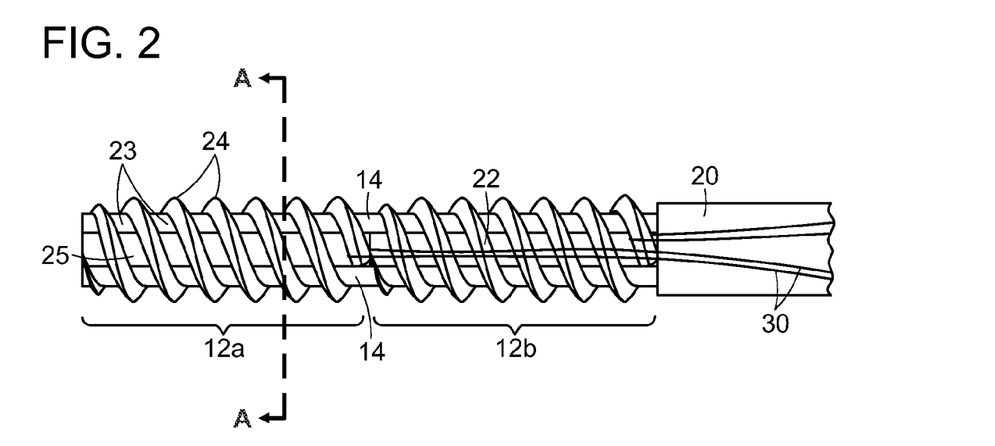
FIG. 2 is a close-up partial side view of the distal region of the embodiment of FIG. 1.

In FIG. 2 the distal end of the delivery device is shown in greater detail. Here, two suture anchors 12a, 12b are slidably mounted and arranged in series upon shaft 14. In the embodiments illustrated in FIGS. 1 to 8, the anchors have a helical-shaped body 22 which includes apertures 23 between turns 24 of the helical body. The apertures 23 permit tissue in-growth by allowing cell- and nutrient-bearing fluids to flow through the anchor. The anchor further includes two support struts 25 (FIG. 3) about which the helical body 22 is disposed. The support struts 45 provide structural rigidity and integrity to the anchor which allow it to be rotational deployment of the anchors.

Figure 3:
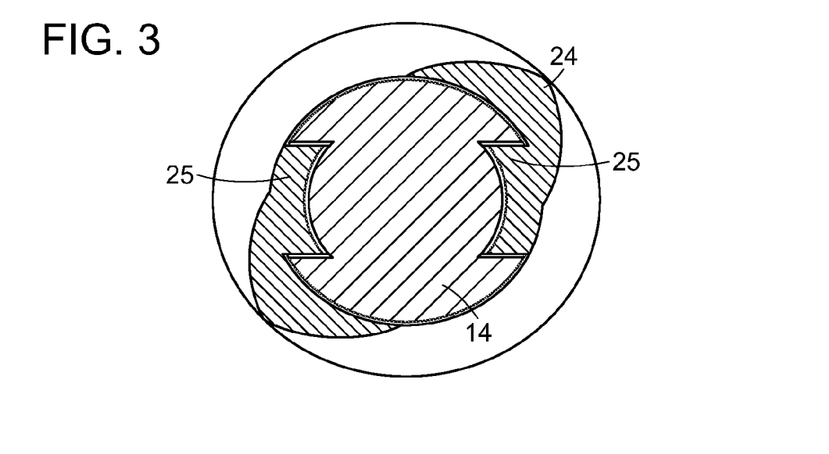
FIG. 3 is a sectional view along the line A-A of FIG. 2.

As can be seen in FIG. 3 (view along the line A-A of FIG. 2), the shaft 14 has a non-circular cross-section. This prevents rotation of the anchor during deployment. In the embodiment shown, the shaft has a generally circular cross-section and includes opposed cut-out regions caused by longitudinal grooves in its outer surface along at least part of its length, which accommodate support struts 25 of the anchors. In alternative embodiments, not shown, the shaft has a polygonal cross section. For example, at least the distal region of the shaft has a triangular, square or hexagonal cross-section. As mentioned above, the non-circular cross-section of the shaft is important for preventing rotation of the anchors during their deployment. The entire shaft may have a non-circular cross-section, although it will be recognised that only the distal region of the shaft, on which the anchors lie, requires a non-circular cross-section to achieve the intended purpose.

Each suture anchor 12 is double loaded with suture 30, which runs from the distal end of the assembly to the handle at the proximal end of the system. The handle further includes suture cleats 32 for securing the free suture ends. In alternative embodiments, not shown, the suture anchor is loaded with a single suture, three, four or more sutures. The suture can be exposed, as shown, or can be threaded through at least a portion of the delivery system, through a lumen or slot in the shaft, or between the shaft and sleeve, for example.

Figure 4:
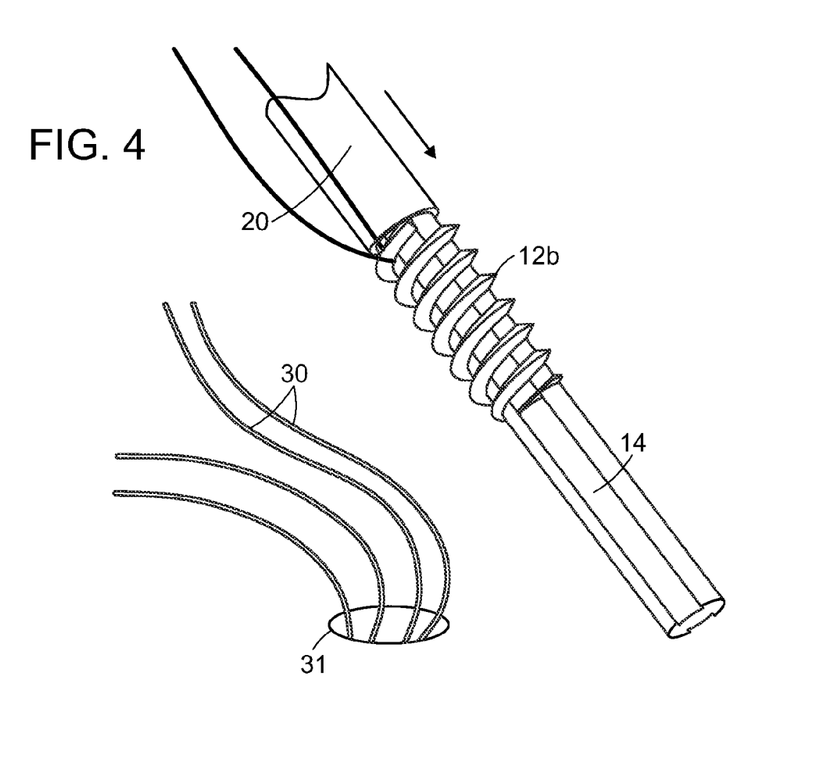
FIG. 4 is a close-up partial perspective view of the distal region of the embodiment of FIG. 1 in which a first surgical anchor has been deployed.
Figure 5:
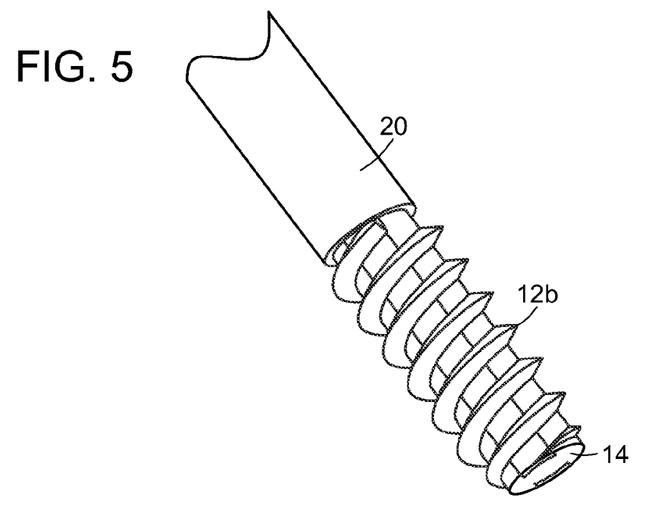
FIG. 5 is a close-up partial perspective view of the embodiment of FIG. 4 in which a second anchor has been advanced distally.
Figure 6A:
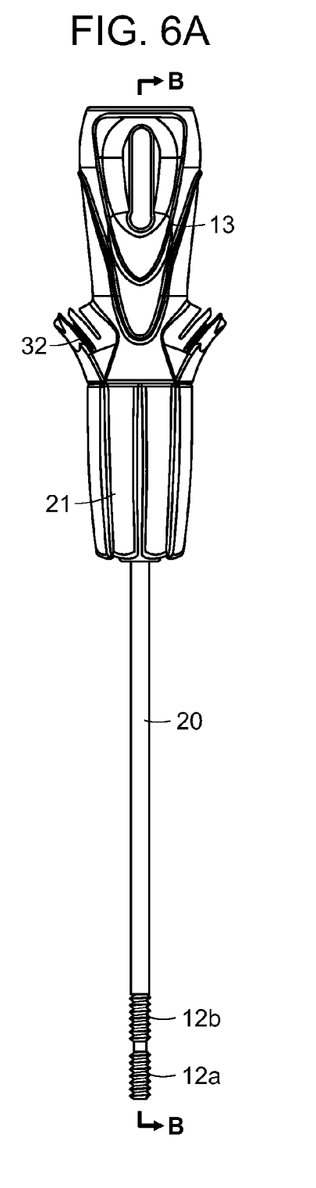
FIGS. 6A-C are side and sectional side views of the embodiment of FIG. 1 before and after deployment of a first surgical anchor.
Figure 6B:
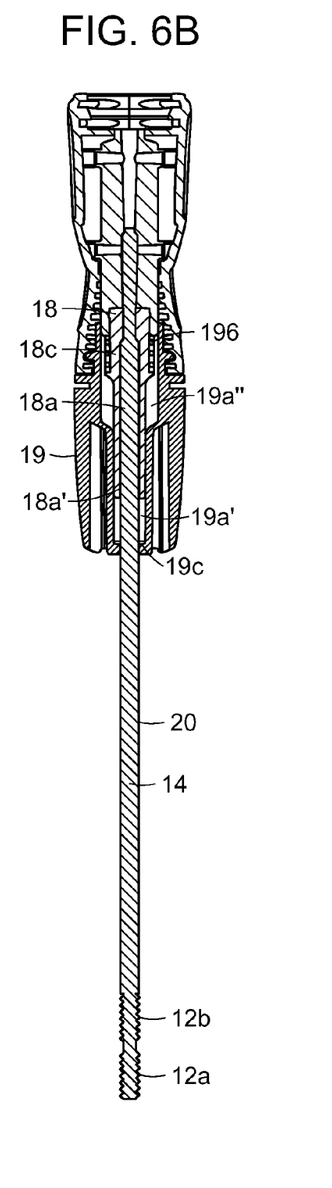
Figure 6C:
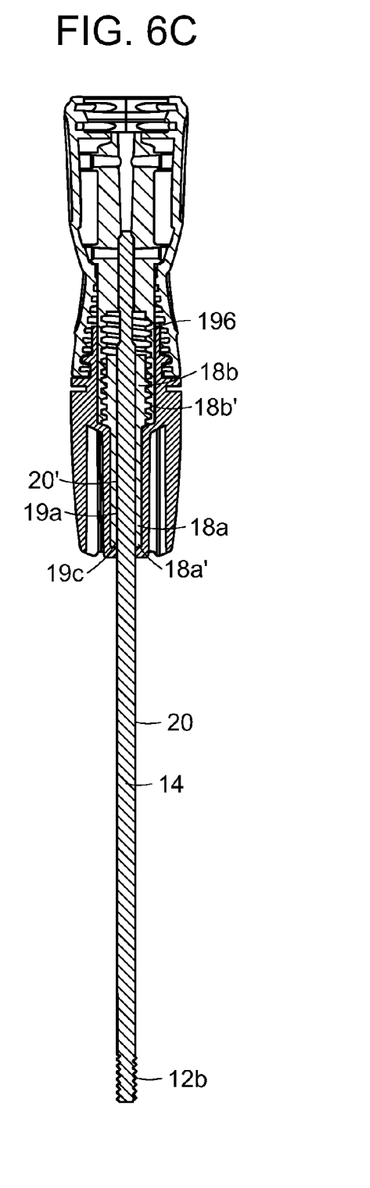

Referring now to FIGS. 4 to 6, in use, the distal-most anchor 12a of the delivery system is rotationally driven directly into bone or into a pre-drilled pilot hole or bone tunnel 31, using the delivery device. As shown in FIG. 4, the first anchor 12a has been deployed into bone (anchor 12a is hidden from view). The delivery device is then removed (FIG. 4), and sleeve 20 advanced distally by rotating driver 21. During this process the sleeve 20 abuts against the proximal end of anchor 12b and, as it moves distally, pushes anchor 12b to the end of shaft 14 ready for its subsequent deployment (FIG. 5).

FIGS. 6B and 6C provide sectional side views of the delivery system along the line B-B of FIG. 6A before and after deployment of the distal most-anchor 12a, and subsequent advancement distally of the proximal-most anchor 12b to a position ready for its deployment.

Shaft 14 is secured within the proximal region of handle 13. As shown, driver 21 includes an inner hub 18 and an outer hub 19, both of which are mounted coaxially with shaft 14. A proximal portion 20' of sleeve 20 is coupled to the outer hub 19 via inner hub 18. The inner hub 18 includes a distal portion 18a, a proximal portion 18b, and a cannulation 18c. The inner hub proximal portion 18b includes threads 18b' on its outer surface. The inner hub 18 is located in a cavity 19a of the outer hub 19. The cavity 19a includes a distal portion 19a' and a proximal portion 19a". The proximal portion 19a" includes threads 19b that engage the threads 18b' on the proximal portion outer surface of inner hub 18. Due to the threaded engagement between threads 18b' and threads 19b, rotation of driver 21, and thus outer hub 19, causes the sleeve 20 to move axially along the length of the shaft 14. Rotation of the outer hub 19 is discontinued when the distal-most anchor, post-deployment of the previously distal-most anchor, is positioned on the distal end of the shaft ready for deployment, or when an end 18a' of the inner hub distal portion 18a engages an end 19c of the cavity distal portion 19a'. This last condition is met when the proximal-most anchor has been advanced and is positioned on the distal end of the shaft ready for deployment.

Figure 7A:
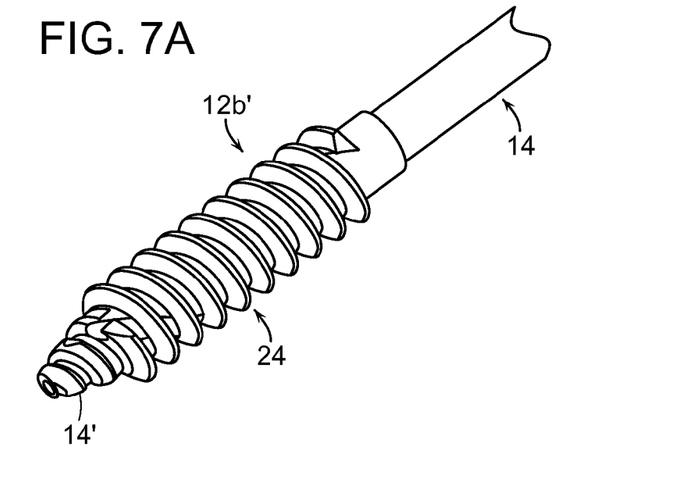
FIGS. 7A&B are close-up partial views of the distal tip of a delivery system shaft according to a second embodiment of the invention.
Figure 7B:
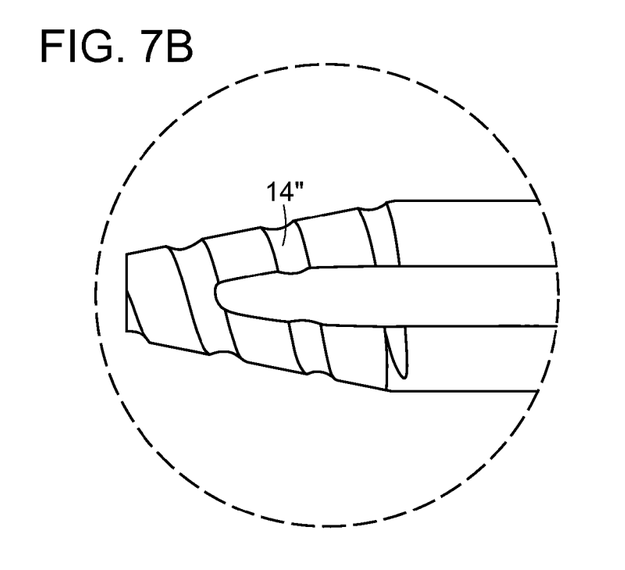

Referring now to FIGS. 7A and 7B, there is shown a shaft 14 having a modified tapered distal tip 14' which includes a helical thread 14" having the same thread pattern as the illustrated anchor 12b'. This feature is intended to aid insertion of the anchor directly into bone without the need for a pre-drilled pilot hole, or with minimal hole preparation.

Figure 8A:
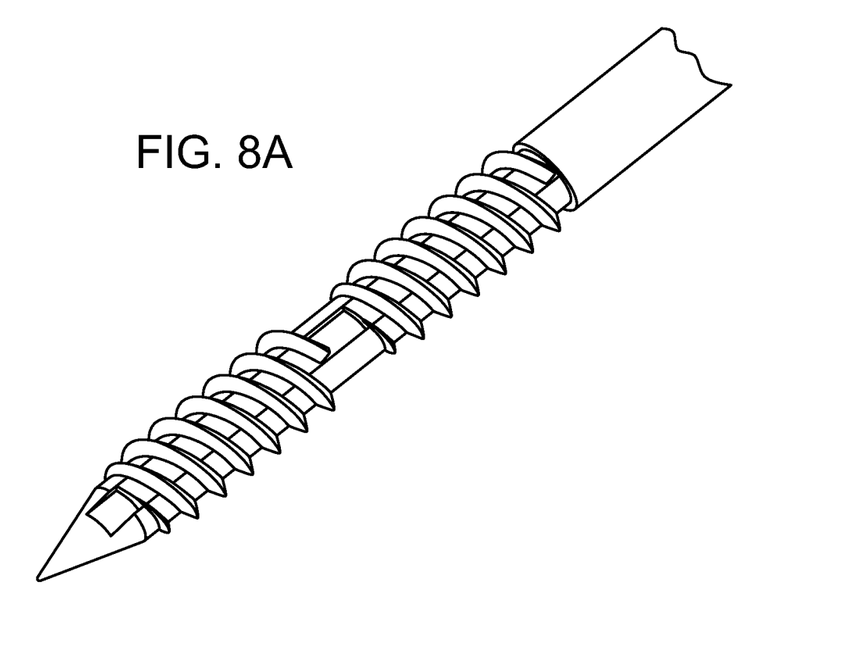
FIGS. 8A&B are close-up partial views of the distal tip of a delivery system shaft according to a third embodiment of the invention.
Figure 8B:
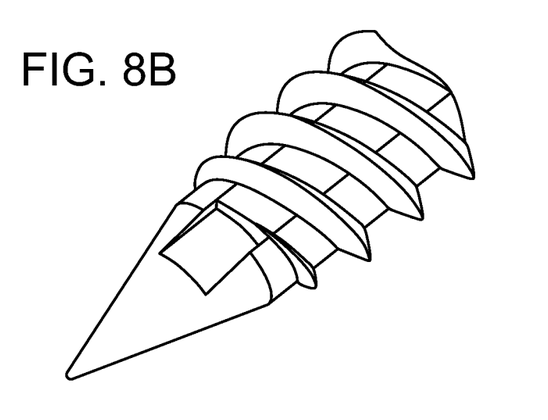

FIGS. 8a and 8B show an alternative shaft tip design in which the tip is pointed. The pointed tip may be sharp or blunt.

Figure 9:
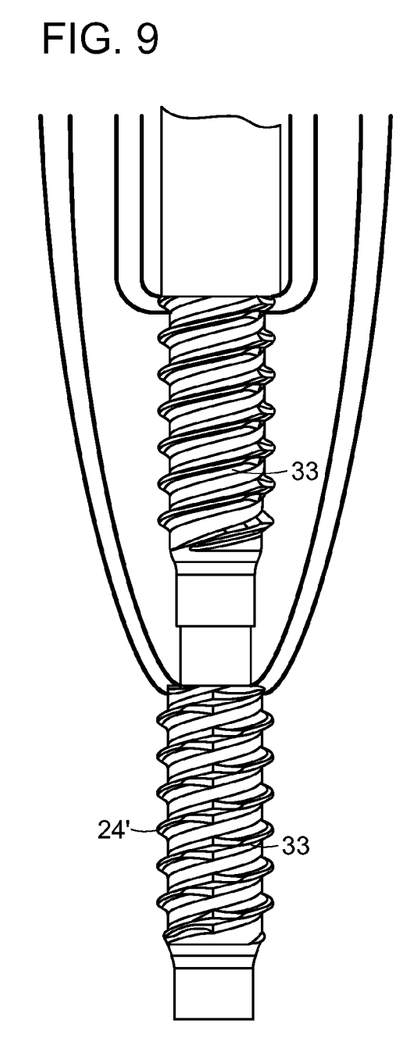
FIG. 9 is a close-up partial view of the distal region of a delivery system according to a fourth embodiment of the invention.

In FIG. 9 there is shown the distal region of a delivery system having alternative non-fenestrated helically threaded anchors 33, in which no apertures are present between turns 24'.

Figure 10:
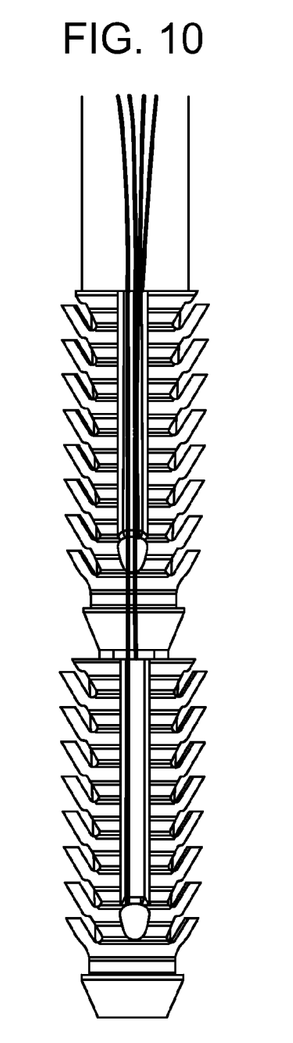
FIG. 10 is a close-up partial view of the distal region of a delivery system according to a fifth embodiment of the invention.

The distal region of a further alternative delivery system is illustrated in FIG. 10. According to this embodiment, the anchors are of the pound-in type in which the anchors are advanced into bone by hammering or pounding the proximal end of the handle of the delivery device, rather than being rotationally driven into bone, as with the previously described embodiments. Anchors according to these embodiments include radial fins, wings or ribs.

Figure 11A:
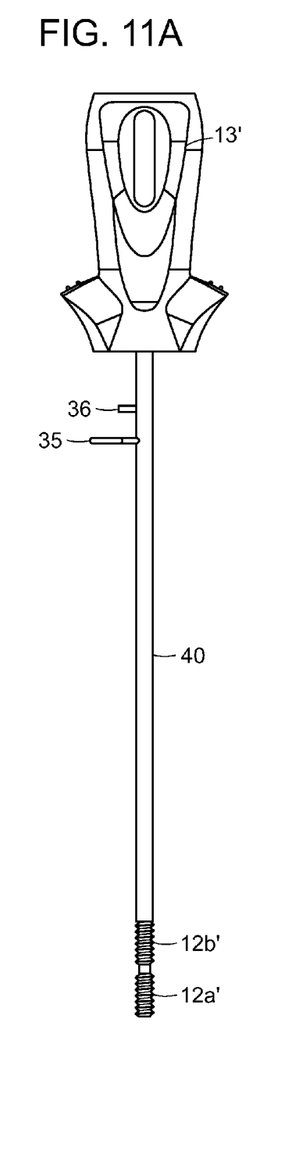
FIGS. 11A-C are side and sectional views of a delivery system according to a sixth embodiment of the invention.
Figure 11B:
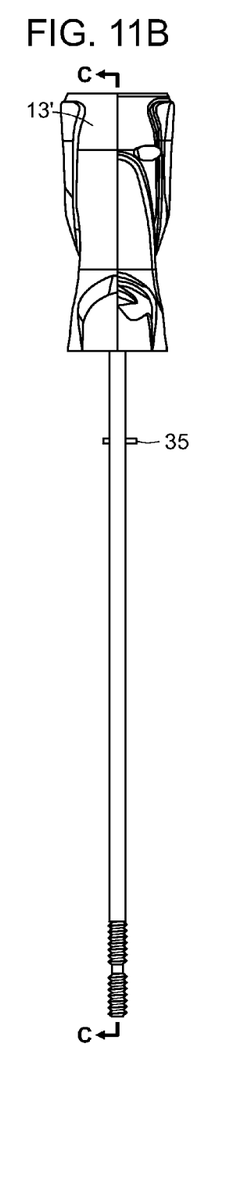
Figure 11C:
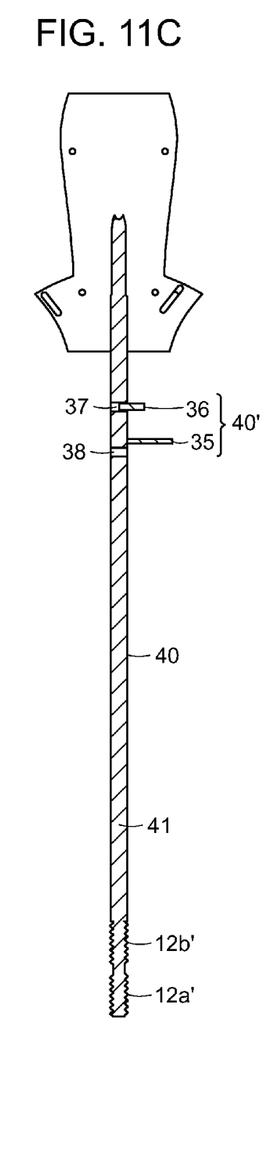
Figure 12A:
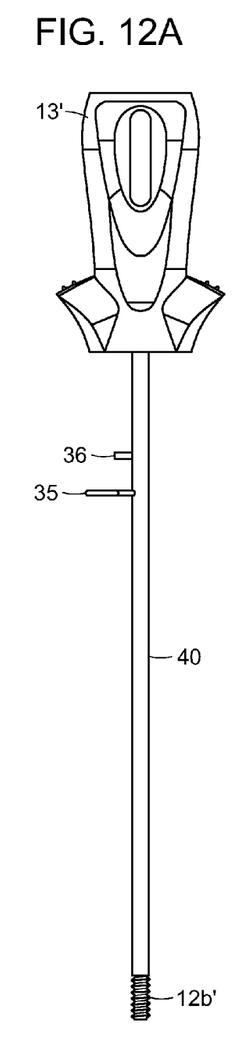
FIGS. 12A-C are side and sectional views of a delivery system of FIG. 10 in which a first surgical anchor has been deployed and a second surgical anchor has been advanced distally.
Figure 12B:
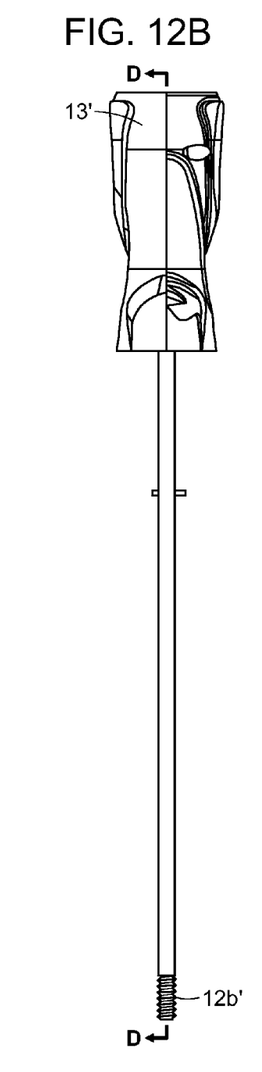
Figure 12C:
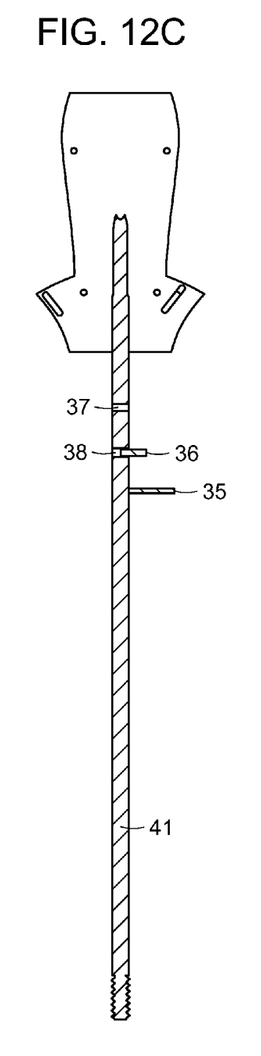

Referring now to FIGS. 11 and 12, there is shown a delivery device having an alternative advancer mechanism. The delivery device includes a proximal handle 13' having a shaft 41 extending therefrom, two suture anchors 12a', 12b' mounted in series at the distal end of shaft 41, and a mechanism for advancing the anchors distally. According to this embodiment, and as shown along sections C-C and D-D, shaft 41 is secured within the proximal region of handle 13'. The delivery device includes a sleeve 40 slidably mounted on shaft 41, and coupled at a proximal portion 40' to the shaft 41 by engagement of connecting pin 36 with shaft aperture 37. Prior to deployment of the distal-most suture anchor 12a', the sleeve 40 is fixed in a first position with respect to the shaft 41 by engagement of connecting pin 36 with shaft aperture 37, as depicted in FIGS. 11A-11C. Upon insertion of the distal-most suture anchor 12a' into the repair site, connecting pin 36 is temporally disengaged from shaft aperture 37, and the shaft 41, and sleeve 40 is indexed axially by pushing knob 35, which is mounted on sleeve 40, such that anchor 12b' is moved to the distal end of shaft 41. Once anchor 12b' has been correctly positioned at the distal end of the shaft, the position of sleeve 40 is fixed relative to shaft 41 by the engagement of connecting pin 36 with a second shaft aperture 38, as shown in FIGS. 12A-12C.

The described delivery system is preferably a sterile, single use delivery device having multiple suture anchors loaded on a single drive shaft. The delivery system is intended for surgical anchors which allow a driver to pass directly through them. The distal-most anchor can be replaced by an anchor which includes a partial cannulation and a solid tip. In the illustrated embodiments, the sutures are attached to the proximal end of each anchor. In alternative embodiments, not shown, the suture is attached to the anchor in its proximal region, or anywhere between the distal and proximal ends of the anchor. The proximal anchors may be advanced to the tip of the shaft of the delivery device using the described rotational mechanism or by means of the described indexer which can be advanced distally and locked once the distal-most anchor has been deployed and the next most-distal anchor has been advanced to the end of the delivery device shaft. The pusher mechanism can include a ratchet mechanism, and/or suitable rod and slot mechanism with appropriate engaging pins.

The components of the anchor assembly, and the handle and hubs of the delivery device, can be formed from a polymer material and by an injection moulding process. However, other materials and processes may be used. The handle and hubs are coupled via an interference fit, although other processes of coupling may be used. The components of the shaft can be made from a metal material via an extrusion or drawings process, and are coupled to the handle and hubs via a threaded fit or an interference fit. Other suitable materials, and methods of coupling may also be used Rather than a sleeve bearing on the proximal end of the anchor, the anchor can be advanced down the shaft by other indexing mechanisms.

In configurations other than proximal suture attachment, suture slots are added to the exterior of the anchor to accommodate the suture.

This invention allows for multiple anchors to be deployed from a single delivery device, without the need for reloading, which would be extremely difficult in the surgical theatre given the small nature of these kinds of devices. This potentially reduces procedural time as the number of sterile implants opened and introduced to the surgical field is reduced. In addition, the system reduces the amount of waste generated per procedure by reducing the quantity of disposable instrumentation and packaging thereby supporting green initiatives and sustainably concerns.

The invention claimed is:

1. A surgical anchor delivery system comprising:
   a delivery device comprising a shaft and a handle;
   an advancer for advancing a surgical suture anchor distally along the shaft; and
   a plurality of surgical anchors serially loaded upon the shaft one in front of the other along a longitudinal axis of the shaft;
   wherein at least one of the plurality of surgical anchors comprises a lumen and one or more longitudinally extending support struts, wherein the lumen enables slidably mounting the at least one of the anchors on the shaft via the shaft passing through the lumen and wherein the delivery device shaft comprises one or more longitudinal grooves in its outer surface adapted for engaging the one or more support struts thereby preventing the at least one of the anchors from rotating relative to the shaft when slidably mounted on the shaft via the lumen.

2. A delivery system according to claim 1, wherein at least one of the plurality of surgical anchors comprises a lumen which extends through a longitudinal axis of the anchor, wherein the lumen is enables slidably mounting the at least one of the anchors on the shaft via the shaft passing through the lumen.

3. A delivery system according to claim 2, wherein one of the plurality of surgical anchors comprises a closed distal end and a lumen which extends through a part of the longitudinal axis of the anchor, wherein the lumen of the anchor with the closed distal end enables slidably mounting the anchor with the closed distal end on a distal tip of the shaft via the shaft passing through the lumen.

4. A delivery system according to claim 1, wherein at least one of the plurality of surgical anchors comprises a lumen, wherein the lumen enables slidably mounting the at least one of the anchors on the shaft via the shaft passing through the lumen and wherein a distal region of the delivery device shaft comprises a non-circular section adapted for preventing the at least one of the anchors from rotating relative to the shaft when slidably mounted on the shaft via the lumen.

5. A delivery system according to claim 1, wherein the delivery device shaft comprises one of more of (i) a lumen, or (ii) one or more longitudinal slots or grooves in its outer surface, wherein the lumen and/or slots or grooves are adapted for channeling a suture attached to a first of the anchors loaded upon the shaft so as to help prevent snagging of the suture.

6. A delivery system according to claim 1, wherein the delivery device shaft comprises a pointed distal tip.

7. A delivery system according to claim 1, wherein the advancer comprises a tubular member or sleeve slidably mounted on the delivery device shaft, proximally of the most proximal surgical anchor.

8. A delivery system according to claim 7, wherein the advancer further comprises a drive mechanism for advancing the tubular member or sleeve distally over the shaft.

9. A delivery system according to claim 8, wherein the drive mechanism includes a knob rotationally mounted on the shaft, wherein the tubular member or sleeve comprises a threaded proximal region and the knob engages the threaded proximal region.

10. A delivery system according to claim 7, wherein the tubular member or sleeve is coupled to a pin or tab configured for selectively engaging and disengaging with one or more detents or apertures in the shaft so as to enable selectively preventing axial movement of the tubular member or sleeve relative to the shaft.

11. A delivery system according to claim 10, wherein the pin or tab is coupled with an indexer with enables predefined distal advancement of the tubular member or sleeve relative to the shaft.

12. A delivery system according to claim 7, wherein a distal end of the tubular member or sleeve abuts against a proximal surface of the most proximal surgical anchor, whereby advancing the tubular member or sleeve distally simultaneously advances the plurality of anchors distally along the shaft.

13. A delivery system according to claim 12, wherein the anchors abut against each other thereby preventing a most distal anchor from sliding back proximally during when the most distal anchor is in a deployment position at the distal end of the delivery device shaft.

14. A delivery system according to claim 7, wherein the tubular member or sleeve includes a knob directly mounted thereon enabling direct manual advancement of the tubular member or sleeve relative to the shaft by pushing on the knob.

15. A delivery system according to claim 1, wherein the advancer comprises a ratchet mechanism for distally advancing the tubular member or sleeve.

16. A delivery system according to claim 1, wherein the advancer comprises a rod which is moveable within a longitudinal channel formed within the delivery device shaft.

17. A delivery system according to claim 16, wherein the rod comprises a radially extending pin which projects from the longitudinal channel and abuts against a proximal end of a most proximal of the plurality of surgical anchors, whereby advancement of the rod translates the pin within the longitudinal channel thereby advancing the surgical anchors distally along the shaft.

18. A delivery system according to claim 1, wherein the handle comprises one or more suture cleats.

19. A delivery system according to claim 1, wherein the surgical anchors are loaded with suture.

20. A delivery system according to claim 1, wherein the surgical anchors are connected to each other by an adjustable suture which comprises slip-knot.

21. The delivery system according to claim 1, wherein at least one of the plurality of surgical anchors the surgical anchors includes a fenestrated helical-shaped body defining apertures between turns of the helical body.

22. The delivery system according to claim 21, wherein the at least one of the plurality of surgical anchors further includes a pair of longitudinally extending support struts about which the helical body is disposed, the support struts configured to provide structural rigidity to the anchor.

23. A delivery system according to claim 1, wherein the anchors abut against each other, whereby the advancer is configured to advance the plurality of anchors along the longitudinal axis of the shaft by pushing a proximal most anchor so as to enable positioning a distal most anchor into a ready for deployment position where the distal most anchor is positioned at the distal end of the delivery device shaft.

* * * * *